US007198757B2

(12) United States Patent
Chiarin

(10) Patent No.: US 7,198,757 B2
(45) Date of Patent: Apr. 3, 2007

(54) PROTECTED STOPPER FOR TEST-TUBES

(75) Inventor: Ulisse Chiarin, Arzegrande (IT)

(73) Assignee: Vacutest Kima S.r.l., Arzecrande-PD (IT)

( * ) Notice: Subject to any disclaimer, the term of this patent is extended or adjusted under 35 U.S.C. 154(b) by 0 days.

(21) Appl. No.: 10/462,720

(22) Filed: Jun. 17, 2003

(65) Prior Publication Data

US 2003/0231988 A1 Dec. 18, 2003

(30) Foreign Application Priority Data

Jun. 17, 2002 (IT) ........................... VI2002A0131

(51) Int. Cl.
*B01L 3/14* (2006.01)
*C12M 1/24* (2006.01)

(52) U.S. Cl. ........................ 422/99; 422/102; 422/104; 215/247; 435/288.1; 435/305.3; 435/305.4

(58) Field of Classification Search .................. 422/99, 422/102–104; 435/288.1, 305.3, 305.4; 215/247
See application file for complete search history.

(56) References Cited

U.S. PATENT DOCUMENTS 3,898,046 A * 8/1975 Ikeda ......................... 422/102
4,704,924 A * 11/1987 Echols ......................... 81/3.4
2001/0020607 A1 * 9/2001 Chiarin ....................... 215/247

FOREIGN PATENT DOCUMENTS

| | | |
|---|---|---|
| EP | 0129029 | * 12/1984 |
| FR | 2.040.666 | * 1/1971 |
| WO | 89/09735 | * 10/1989 |

* cited by examiner

*Primary Examiner*—Lyle A. Alexander
(74) *Attorney, Agent, or Firm*—Browdy and Neimark, PLLC

(57) ABSTRACT

Protected stopper for test-tubes, including a substantially cylindrically extending elastomer inner body arrangeable to close a test-tube including a sealing portion formed to be inserted inside the mouth of the test-tube and a collar piece connected above the sealing portion and projecting radially with respect to the latter to receive, in bearing contact therewith, the mouth of said test-tube. The stopper includes a substantially cylindrical cover, closed at the top and mounted to cover the inner body. An engaging mechanism for simultaneously securing the inner body to the cover and the stopper to the test-tube are included, consisting of a plurality of projections extending on the inside of the side wall of the cover, coming into contact with the outer wall of the test-tube and spaced from the closing wall of the cover to form a contact step capable of constraining the projecting collar piece of the inner body.

12 Claims, 3 Drawing Sheets

PROTECTED STOPPER FOR TEST-TUBES

TECHNICAL FIELD

The present invention relates to a protected stopper able to be fitted onto test-tubes which can be used in analysis laboratories, for example for blood samples or for handling biological liquids.

Traditionally, these test-tubes define a containing chamber inside which a suitable degree of vacuum has been established beforehand in order to allow suction of the biological liquid inside it.

As is known, at the moment of extraction of the stopper, owing to the effect of the vacuum contained inside the test-tube, some of the liquid escapes in the form of droplets and may soil the hands of the technician or surrounding areas.

BACKGROUND ART

In order to overcome this drawback, for some time now so-called "protected" stoppers for test-tubes have been introduced, said stoppers being provided with a cover which covers both the stopper and the top part of the test-tube.

In practice, this protected stopper consists of two parts which are secured together:

- an elastomer inner body, for example made of butyl rubber (the actual stopper), which is used to close the test-tube and able to be perforated so as to allow the introduction of the syringe needle;
- a cover, outside the abovementioned body, which is made of suitably rigid plastic material, for example polyethylene.

According to the present state of the art various types of protected stoppers are known.

By way of example reference is made to the protected stopper described in European Patent No. 129,029 which is configured so that the cover has, on the inner wall facing the inner body, an annular groove inside which a corresponding relief projecting from the abovementioned inner body is inserted.

The protected stopper described above and other similar stoppers of the known type have the drawback that the body of the cover has undercuts for securing the inner body such that the operation of injection-moulding of the stopper itself is difficult and complicated.

Moreover, the presence of an undercut in the form of grooves on the wall of the cover results in the need for a sufficiently large thickness of the said wall, which is in contrast with the need to limit the extension of the stopper beyond the external diameter of the test-tube in order to keep the dimensions as small as possible and allow insertion of the assembled test-tube, i.e. complete with stopper, inside the holders or other adapters of analysis machines.

European Patent EP 0,419,490 attempted to overcome these drawbacks by securing together the components of the protected stopper using two extensions which project from the internal cylindrical surface of the cover in the direction of the longitudinal axis and which define a groove inside which an annular relief projecting from the inner body is inserted in a retaining relationship. In accordance with this solution, the bottom extension of the cover is positioned between the front part of the test-tube and the annular relief of the inner body.

This configuration involves, however, involves part of the inner body of the stopper having to extend necessarily outside the test-tube in order to form the connection with the cover. Since the length of the inner body of the stopper normally has a predefined value which cannot be modified, in that it is related to the length of the syringe needle, the frictional force between stopper and test-tube which ensures a sealed closure is consequently also reduced in a disadvantageous manner.

DISCLOSURE OF THE INVENTION

The object of the present invention is therefore that of overcoming the problems of stoppers of the known type mentioned above by providing a protected stopper for test-tubes, comprising an elastomer inner body and a plastic cover having an external wall slightly exceeding the diameter of the test-tube.

A further object of the invention is that of providing a protected stopper in which the cover may be made by means of injection-moulding using simple moulds which do not give rise to extraction problems.

A further object of the invention is that of providing a protected stopper where assembly of the two parts, i.e. insertion of the inner body in the cover, is rapid and reliable.

A further object of the invention is that of providing a protected stopper in which the cover is always in contact with the external top portion of the test-tube, in order to increase securing of said stopper on said test-tube, without having to use screw-type or hook-type closing systems.

A further object of the present invention is that of providing a protected stopper which is constructionally simple, operationally entirely reliable and produced at a cost which is less than that of protected stoppers of the known type.

These and other objects are achieved by the protected stopper for test-tubes according to the present invention which comprises: a substantially cylindrically extending elastomer inner body which can be arranged so as to close a test-tube and which comprises a sealing portion formed so as to be inserted into the mouth of the test-tube and a collar piece connected above the sealing portion and projecting radially with respect to the latter so as to receive, in bearing contact therewith, the mouth of the test-tube; a cover made of plastic with a substantially cylindrically extending side wall, at least partly delimited at one end by an upper closing wall, the cover being able to be arranged so as to cover the inner body and a top part of the test-tube when the stopper is engaged thereon and having engaging means for simultaneously securing the inner body to the cover and the whole stopper on the test-tube.

According to the invention, the stopper is characterized in that the engaging means consist of a plurality of projections which extend on the inside of the side wall of the cover so as to make contact with the outer wall of the test-tube, said projections being spaced from the closing wall of the cover and being able to form a contact step capable of constraining the projecting collar piece of the inner body.

Advantageously, the distance of the contact step formed by the projections from the closing wall of the cover is greater than the thickness of the collar piece so as to allow the test-tube to come into contact against the collar-piece without any interference of the said projections.

Advantageously, the projections retain the collar piece of the inner body by means of the contact step and, by means of a resilient action on the outer wall of the test-tube, keep the stopper secured on the said test-tube.

BRIEF DESCRIPTION OF THE DRAWINGS

These objects, together with others, are all achieved by the stopper in question, the technical characteristics of which may be clearly determined from the contents of the claims below and the advantages thereof will emerge more clearly from the following detailed description, provided with reference to the accompanying drawings, which show some purely exemplary non-limiting embodiments in which:

DETAILED DESCRIPTION OF A PREFERRED EXAMPLE OF EMBODIMENT

Figure 1:
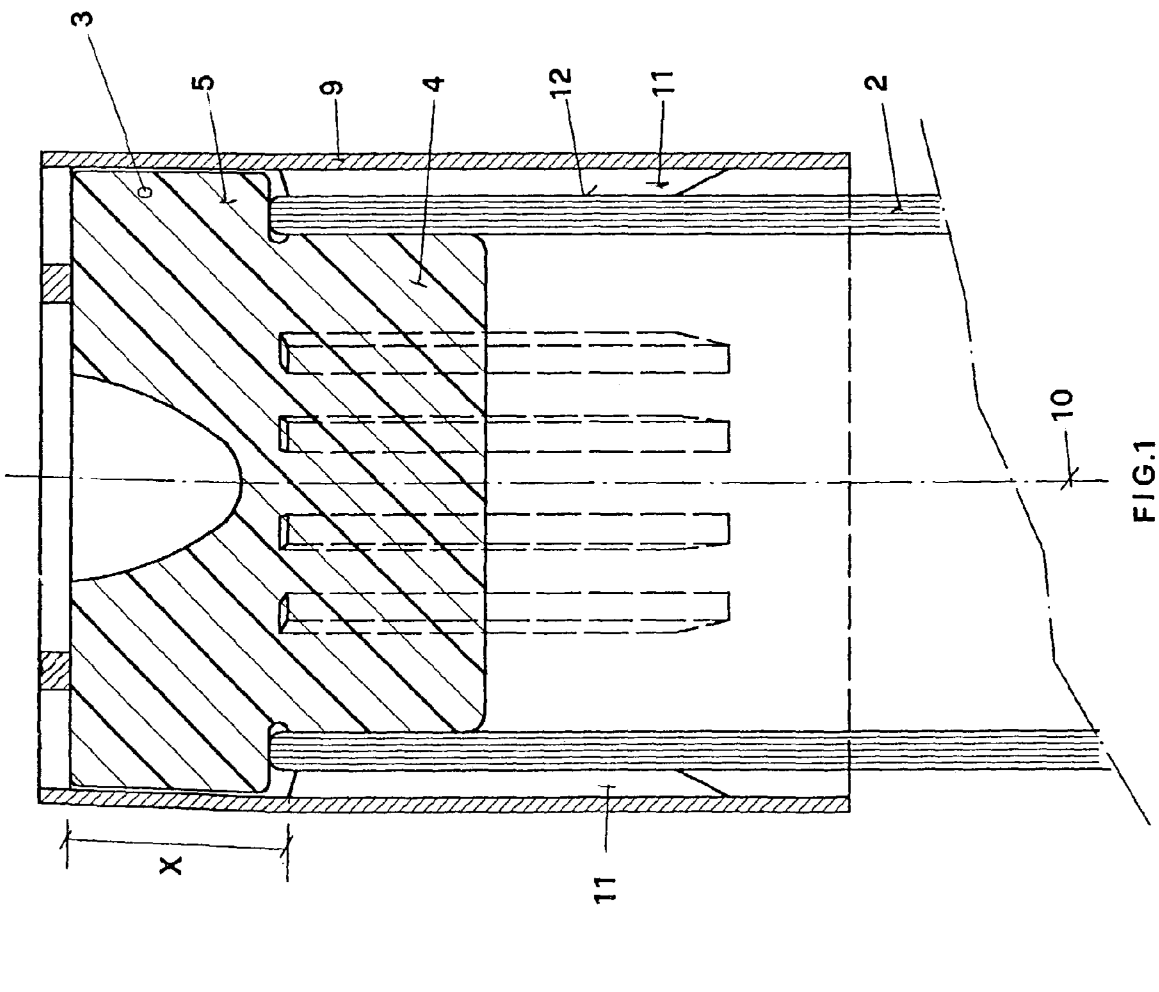
FIG. 1 shows a cross-sectional view of the stopper according to the invention mounted on a test-tube.
Figure 5:
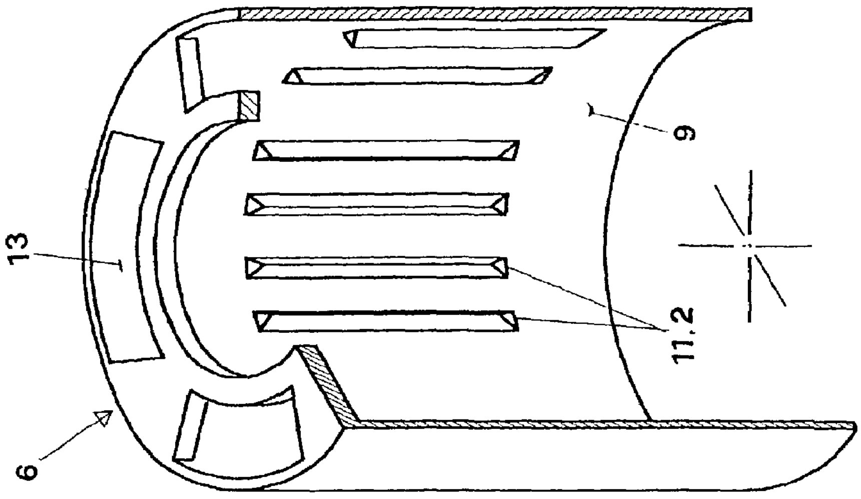
FIGS. 3 to 8 show partially sectioned perspective views of some possible embodiments of the cover of the stopper according to FIG. 2.
Figure 4:
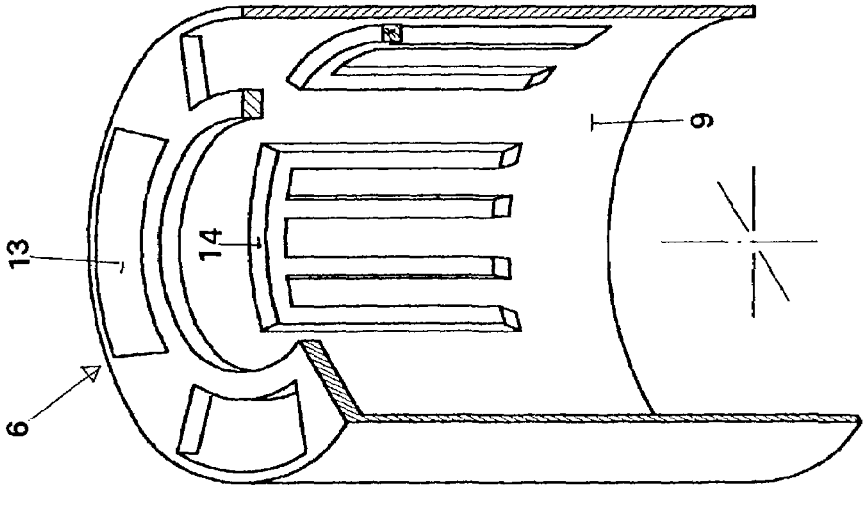

As can be seen in FIG. 1, the protected stopper, which is denoted in its entirety by 1, for closing the test-tube 2, comprises a substantially cylindrically extending inner body 3 made of an elastomer, such as rubber or the like, with a sealing portion 4 thereof able to be inserted into the mouth of the test-tube, and a radially projecting upper collar piece 5 against which the top part of said test-tube 2 is closed.

The stopper 1 is completed by a compact plastic cover 6 with a substantially cylindrically extending side wall delimited at the top by a closing wall 7.

The cover 6 is intended to contain the inner body 3 and the top part of the test-tube 2. The closing wall 7 is provided with a central opening 8 for allowing the insertion of a syringe needle.

According to the invention, from the inside of the circumferential wall 9 there extend, advantageously in a radial direction towards the longitudinal axis 10, projections 11 which are able to come resiliently into pressing contact against the external wall 12 of the test-tube 2 so as to ensure securing of said stopper on said test-tube.

For this purpose, the top part of the projections defines a circumference inside the stopper 1 having a diameter slightly smaller than that of the external wall of the test-tube, so as to ensure, once the test-tube 2 is assembled, mechanical interference between the projections 11 of the cover 6 and the test-tube 2.

The interference occurs with a frictional force having an intensity sufficient to ensure sealing of the stopper 1 on the test-tube 2 and at the same time allows a technician to remove the stopper 1 without particular difficulty.

As can be seen in FIG. 1, the projections 11, which have a substantially longitudinal extension, terminate at a distance “X” from the closing wall 7 of the cover 6. This distance is greater than the thickness of the collar of the inner body 3.

This enables the inner body 3 to be sealed inside the test-tube 2 with the mouth of the latter resting against the collar piece 5 of the inner body 3 without there being any interference due to the presence of the projections 11 which by means of their contact step ensure retaining of the said collar piece 5 on the cover 6.

Figure 2:
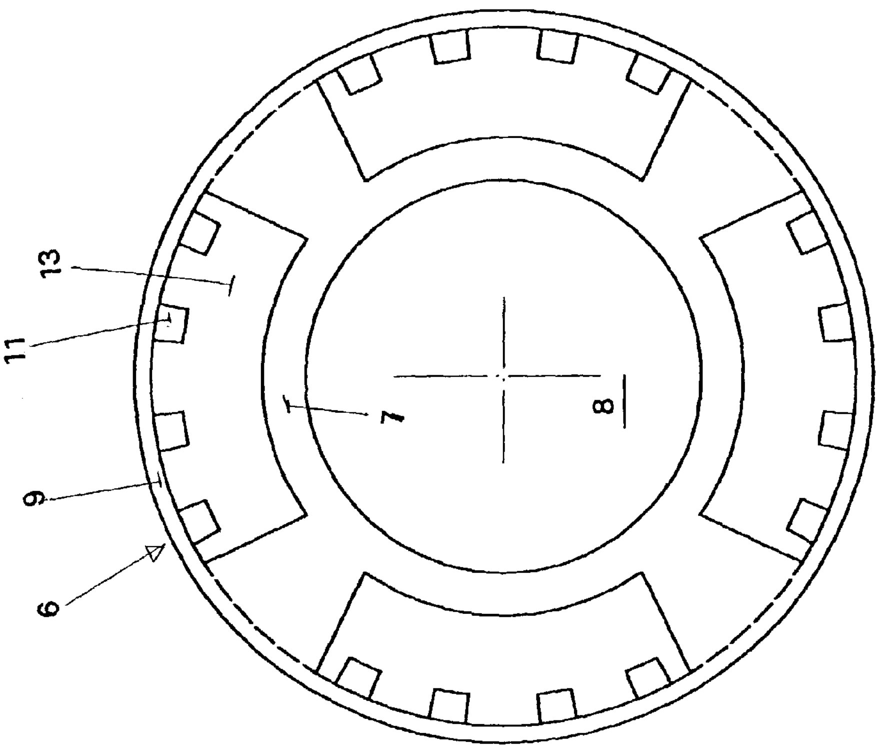
FIG. 2 shows a top plan view of an enlarged detail of the stopper according to FIG. 1, relating to a cover.

As can be seen in FIG. 2, the projections 11 are arranged so that the longitudinal axial projection of their cross-section is always contained within openings 13 formed on the closing wall 7 of the cover 6 when viewing said closing wall 7 in plan view.

Advantageously, at least one end of the longitudinal extension of the projections 11 is shaped in a receiving manner so as to favour deformation of the collar piece 5 of the inner body 3 during insertion of the latter inside the cover 6.

The projections may be made of the same material as that from which the side wall of the cover 6 is made or may be made of a different material, for example having different physical properties.

This allows the construction of moulds which are particularly simple and able to ensure the formation of the cover 6 without providing an undercut so as to allow easy extraction of the part from the mould.

Figure 3:
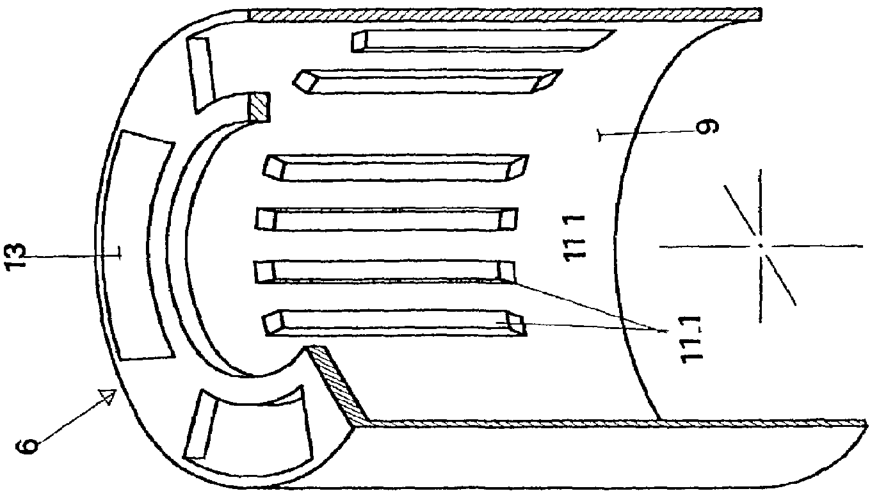
Figure 8:
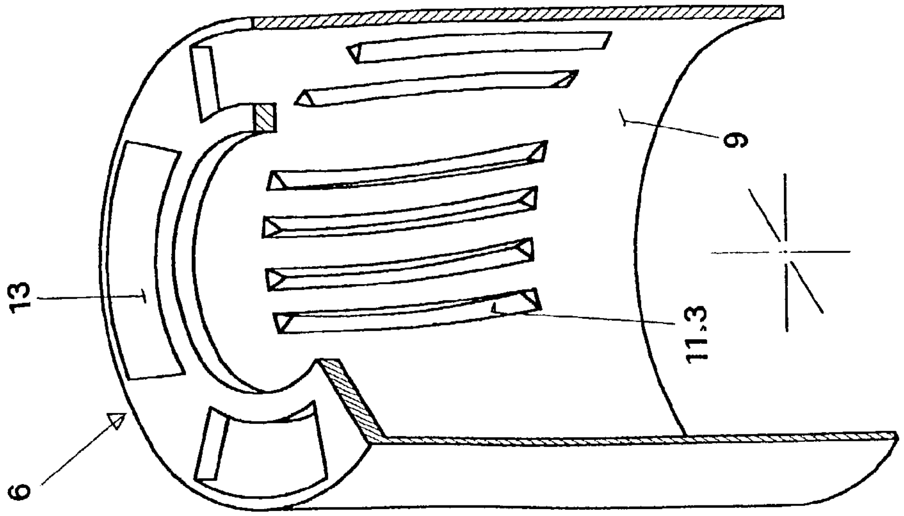
Figure 7:
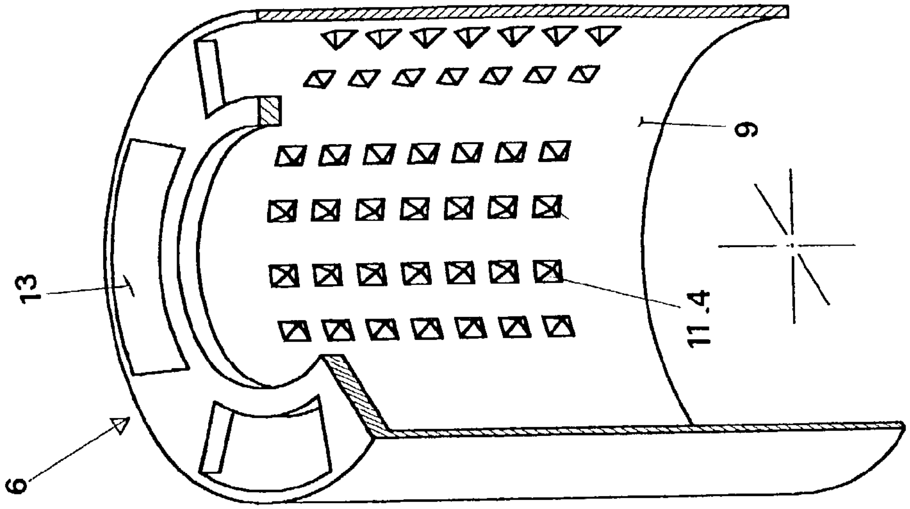
Figure 6:
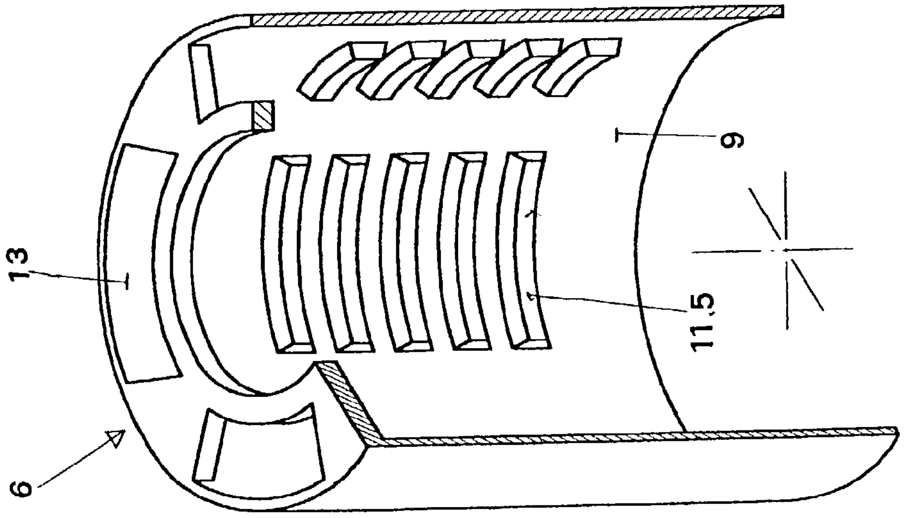

As can be seen in FIG. 3 and the following figures, the projections 11 may assume different forms and for example have a square cross-section 11.1 or a triangular cross-section 11.2. In accordance with the examples of embodiment illustrated in FIGS. 4 to 8, it is possible to envisage projections with a circular progression 14, said projections joining together several longitudinal projections, projections with a curvilinear progression 11.3, projections consisting of a plurality of dot-like elements 11.4 or also projections formed by angular segments 11.5 with a circumferential extension perpendicular to the longitudinal axis of the test-tube.

From that described above it can be understood how the abovementioned objects have been achieved: the cover according to the invention, in its cylindrical side wall 9, does not have cavities but only projections 11, so that the thickness of the said wall 9 may be minimal and not give rise to dimensional or production-related problems since it merely has to satisfy mechanical strength requirements during use.

Obviously embodiments different from those described are possible depending on the requirements, but nevertheless all falling within the scope of the following claims.

The invention claimed is:

1. Protected stopper for test-tubes, which can be used in particular in analysis laboratories, for example for the taking of blood samples or for handling biological liquids, comprising:

a substantially cylindrically extending elastomer T-shaped inner body which can be arranged so as to close and seal a test-tube by entering a mouth of the test-tube, said inner body comprising a sealing portion formed so as to be inserted into the mouth of said test-tube and a collar piece connected integrally to and extending above said sealing portion and projecting radially outwardly with respect to the sealing portion so as to receive, in bearing contact therewith, the mouth of said test-tube thereby closing the mouth of said test-tube;

a cover made of plastic with a substantially cylindrically extending side wall, at least partly delimited at one end by an upper closing wall, said cover being able to be arranged so as to cover said inner body and a top part of said test-tube when said stopper is engaged in said test-tube, said cover having engaging means for simultaneously securing said inner body to said cover and the whole protected stopper on said test-tube, said closing wall of said cover being provided with a central opening for allowing the insertion of a needle;

wherein said engaging means consists of a plurality of projections which extend on the inside of the side wall of said cover so as to make contact with and engage the outer wall of said test-tube when the stopper is engaged in the test-tube, said projections being spaced from said closing wall of said cover and having end portions which form a contact surface ending below the collar piece when the inner body is inserted in the test-tube mouth and being capable of constraining the projecting collar piece of said inner body, wherein the collar piece of the inner body is situated between the contact surface of the projections and the upper closing wall of the cover, wherein the end surface of said projections define an internal circumference having a diameter slightly smaller than that of the external wall of said test-tube so as to ensure, when the test-tube is assembled, interference between the projections of said cover and said test-tube with a frictional force having an intensity sufficient to ensure securing of said stopper on said test-tube, wherein said projections extend, in a radial direction, towards a longitudinal axis of said cover and are able to come into contact resiliently against the external wall of said test-tube, so as to perform securing of said stopper on said test-tube, and wherein the distance of said contact surface from the closing wall of the cover is greater than the thickness of said collar piece.

2. Protected stopper for test-tubes according to claim 1, wherein said projections act by means of said contact surface on said collar piece so as to constrain said inner body to said cover in particular during extraction of said stopper from said test-tube.

3. Protected stopper for test-tubes according to claim 1, wherein said projections extend longitudinally and parallel to the longitudinal axis of said test-tube.

4. Protected stopper for test-tubes according to claim 1, wherein said projections are arranged on the inner wall of said cover opposite openings present on the closing wall of said cover, so that the longitudinal axial projection of a cross-section of said projections is always contained within said openings when viewing said closing wall in plan view.

5. Protected stopper for test-tubes according to claim 1, wherein said projections have at least one of their longitudinal ends shaped in a receiving manner so as to favour the deformation of said collar piece of the inner body during insertion of the latter in the cover.

6. Protected stopper for test-tubes according to claim 1, wherein said projections are made of a material which is different from and/or has physical properties different from a material which forms the side wall of the cover.

7. Protected stopper for test-tubes according to claim 1, wherein said closing wall of said cover is provided with a central opening for allowing the insertion of a syringe needle.

8. Protected stopper for test-tubes according to claim 1, wherein said projections are shaped with a square cross-section or with a triangular cross-section.

9. Protected stopper for test-tubes according to claim 1, wherein said projections have elements for joining together two or more projections.

10. Protected stopper for test-tubes according to claim 1, wherein said projections consist of a plurality of dot shaped elements.

11. Protected stopper for test-tubes according to claim 1, wherein said projections form angular segments with a circumferential extension perpendicular to a longitudinal axis of said test-tube.

12. Protected stopper for test-tubes, which can be used in particular in analysis laboratories, for example for the taking of blood samples or for handling biological liquids, comprising:

a substantially cylindrically extending elastomer T-shaped inner body which can be arranged so as to close and seal a test-tube by entering a mouth of the test-tube, said inner body comprising a sealing portion formed so as to be inserted into the mouth of said test-tube and a collar piece connected integrally to and above said sealing portion and projecting radially outwardly with respect to the sealing portion so as to receive, in bearing contact therewith, the mouth of said test-tube thereby closing the mouth of said test-tube;

a cover made of plastic with a substantially cylindrically extending side wall, at least partly delimited at one end by an upper closing wall, said cover being able to be arranged so as to cover said inner body and a top part of said test-tube when said stopper is engaged in said test-tube, said cover having engaging means for simultaneously securing said inner body to said cover and the whole protected stopper on said test-tube, said closing wall of said cover being provided with a central opening for allowing the insertion of a needle;

wherein said engaging means comprises a plurality of projections which extend on the inside of the side wall of said cover so as to make contact with and engage the outer wall of said test-tube when the stopper is engaged in the test-tube, said projections being spaced from said closing wall of said cover and having end portions which form a contact surface ending below the collar piece when the inner body is inserted in the test-tube mouth and being capable of constraining the projecting collar piece of said inner body;

the distance of said contact surface from the closing wall of the cover is greater than the thickness of said collar piece; and said projections act by means of said contact surface on said collar piece so as to constrain said inner body to said cover in particular during extraction of said stopper from said test-tube, wherein the end surface of said projections define an internal circumference having a diameter slightly smaller than that of the external wall of said test-tube so as to ensure, when the test-tube is assembled, interference between the projections of said cover and said test-tube with a frictional force having an intensity sufficient to ensure securing of said stopper on said test-tube, wherein said projections extend, in a radial direction, towards a longitudinal axis of said cover and are able to come into contact resiliently against the external wall of said test-tube, so as to perform securing of said stopper on said test-tube, and wherein the distance of said contact surface from the closing wall of the cover is greater than the thickness of said collar piece.

* * * * *